United States Patent [19]
Brandhorst

[11] Patent Number: 5,492,243
[45] Date of Patent: Feb. 20, 1996

[54] STERILE CONTAINER

[75] Inventor: Gerd Brandhorst, Munich, Germany

[73] Assignee: Thera Patent GmbH & Co. KG Gesellschaft Fuer Industrielle Schutzrechte, Seefeld, Germany

[21] Appl. No.: 919,402

[22] Filed: Jul. 27, 1992

[30] Foreign Application Priority Data

Jul. 25, 1991 [DE] Germany .................. 9109207 U

[51] Int. Cl.$^6$ ...................................... A61J 1/08
[52] U.S. Cl. ........................ 220/4.21; 220/4.24
[58] Field of Search ............... 220/4.21, 4.24, 220/4.25, 354, 355

[56] References Cited

U.S. PATENT DOCUMENTS

| | | | |
|---|---|---|---|
| 3,117,691 | 1/1964 | Williams | 220/354 X |
| 3,447,711 | 6/1969 | Bozek | 220/4.24 |
| 4,491,238 | 1/1985 | Tobolt | 220/307 |
| 5,103,993 | 4/1992 | Bingisser | 220/355 |

FOREIGN PATENT DOCUMENTS

| | | |
|---|---|---|
| 0040959 | 12/1981 | European Pat. Off. . |
| 0157121 | 10/1985 | European Pat. Off. . |

Primary Examiner—Steven M. Pollard
Attorney, Agent, or Firm—Foley & Lardner

[57] ABSTRACT

The container herein described protects a sterile capsule containing predetermined amounts of a multi-component curable material (such as bone cement) against contamination. The container allows externally applied pressure to be transmitted to the capsule. The material components contained in the capsule are thereby brought into contact and may be mixed in an oscillating mixer. Even when the mixer is not operated in a sterile environment, the capsule remains sterile, which is essential for use such as in an operating room.

For transmitting the pressure required for actuating the capsule, the container consists of two shell portions 1 and 2 which can be moved against each other by application of external compression forces. When the container is opened, the capsule is protected by means of a ring 3 or apron against contacting non-sterile container surfaces.

3 Claims, 2 Drawing Sheets

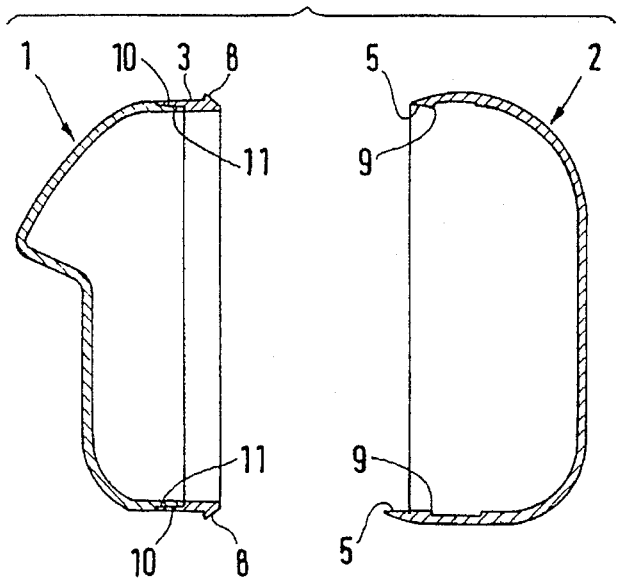
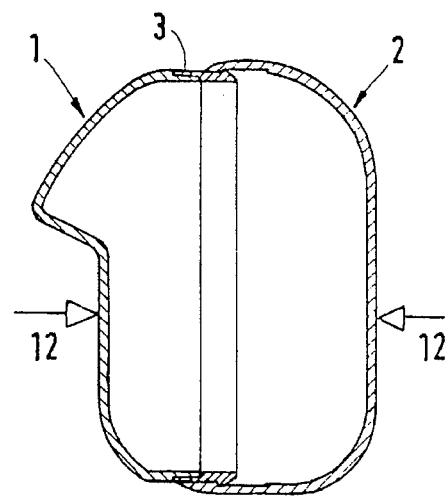
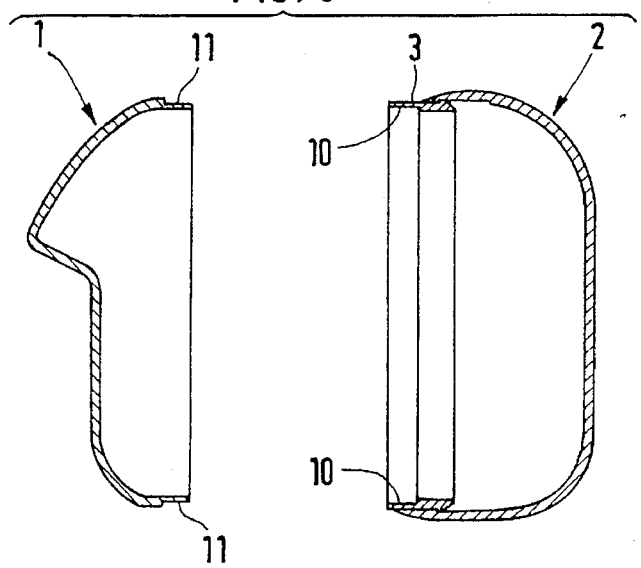

STERILE CONTAINER

BACKGROUND OF THE INVENTION

The invention relates to container for receiving a pressure-actuated sterile capsule for a curable material. Capsules of this type are used for instance in dentistry. They contain predetermined amounts of material components for manufacturing a ready-to-use cement or filler, such as a synthetic resin or amalgam.

A capsule of this type is described in EP 0157121 A1. It contains a powdery component and, in a foil bag, a liquid component. In use, pressure is exerted on the capsule by means of a pair of pliers so that the foil bag is torn open and the liquid comes into contact with the powder. The two components are then mixed to react with each other. The completely mixed, ready-to-use preparation may then be applied directly to the location to be treated, such as a tooth cavity, where it hardens.

The use of the capsule described above is advantageous in that the prescribed mixing ratio of the components is always accurately maintained. The curing time and the properties of the cured material are therefore always constant and exactly known.

The use of such capsules has been restricted essentially to dentistry where there are specific requirements concerning the sterility of the outer capsule surface.

There is great demand, also in other medical areas, of curable materials, the components of which must be provided in accurate amounts. This applies specifically to surgery where bone cement is often required for implanting protheses etc.

However, electrical mixers are normally unsuited for use in the operating room because they cannot be sterilised any desired number of times. Both, heat treatment and chemical sterilization would impair the motor and the electronic control. In view of the short time interval available for the cement to cure, it is further impossible to place the mixer outside the operating room and to sterilize the capsule after the mixing process and before it is taken into the operating room.

A container for receiving a capsule which holds a liquid for mixing with a powder contained in another section of the container is known from EP 0040959 A1. The container comprises a cylindrical vessel and a cap which includes interior fingers and is movable along the axis of the vessel to urge the ends of the fingers in between the capsule and the inner container wall, thereby breaking the capsule. The powder and liquid are then mixed by shaking and the mixture dispensed. This container is unsuited for handling by conventional mixers. Further, the capsule is never removed from the container but discarded with it. No means are provided for ensuring the sterility of the contents once the container is opened.

SUMMARY OF THE INVENTION

It is an object of the invention to provide a device which permits the use of the capsule described above in an environment of high sterile requirements. Conventional pressure pliers and mixers should be useable.

This object is met by a container which includes two sterile-sealing shell portions adapted to slide against each other when compressed and thereby transmitting pressure to the capsule, and to be opened for subsequent removal of the capsule, and means for protecting the capsule, when the shell portions are opened, against contact with that surface of one of the shell portions which, when the shell portions are moved against each other, slides on an outer surface of the other shell portion.

This container receives the capsule which has been completely, i.e. also externally, sterilized, and protects it against germs and impurities. The capsule in the container may thus be conveniently handled even in a non-sterile environment. The container may be made with walls to thin that it can be accommodated in the holders of conventional oscillating mixers which are otherwise dimensioned to hold the capsule without a container. The container further serves to transmit the pressure from the pliers or activator to the capsule.

The pressure pliers and mixer may be used outside the operating room. After mixing, the sterile capsule is removed from the container within a sterile sluice and brought into the operating room in sterile condition.

In a preferred embodiment, the protecting means includes an apron provided on the one shell portion, the apron projecting beyond the rim of the one shell portion and, in the assembled condition, lying between the other shell portion and the capsule. In this embodiment, the capsule is particularly well protected against any contact with non-sterile surfaces of the container when the latter opened. Further, this embodiment is specifically uncomplicated in that it requires only two shell portions.

In another advantageous embodiment, the protecting means includes a ring provided between the shell portions, the ring being connected to the other shell portion and slidable with respect to the one shell portion when the shell portions are moved against each other, and being adapted to disengage from the other shell portion and remaining connected to the one shell portion when the container is opened. Due to the provision of the ring, the location at which the two container halves move relatively to each other to transmit the applied pressure to the inner capsule, is different from the location at which the container is opened. This prevents the capsule, when the container is opened, from contacting any such surface of the one shell portion which slides on the outer surface of the other container half and is thus contaminated when the container is compressed.

It is further advantageous to provide the ring and the one shell portion with cooperating noses which permit a sliding movement between these parts when compressed, the noses causing the ring and the one shell portion to become hooked together when the two shell portions are pulled apart.

According to yet another embodiment, the shell portions upon opening are completely separable from each other, one of the shell portions having its inner side provided with two opposite clamping surfaces for engaging the capsule and, when the container is opened, being adapted to be deformed by pressure exerted on two outer surfaces so as to release the capsule. This results in a convenient handling of the container when removing the capsule.

BRIEF DESCRIPTION OF THE DRAWINGS

FIG. 1 shows a container prior to receiving a capsule.

FIG. 2 shows the same container in the closed condition, with the inner capsule being not shown for clarity.

FIG. 3 represents the re-opened container, from which the capsule has been removed.

DETAILED DESCRIPTION OF PREFERRED EMBODIMENTS

Figure 4:
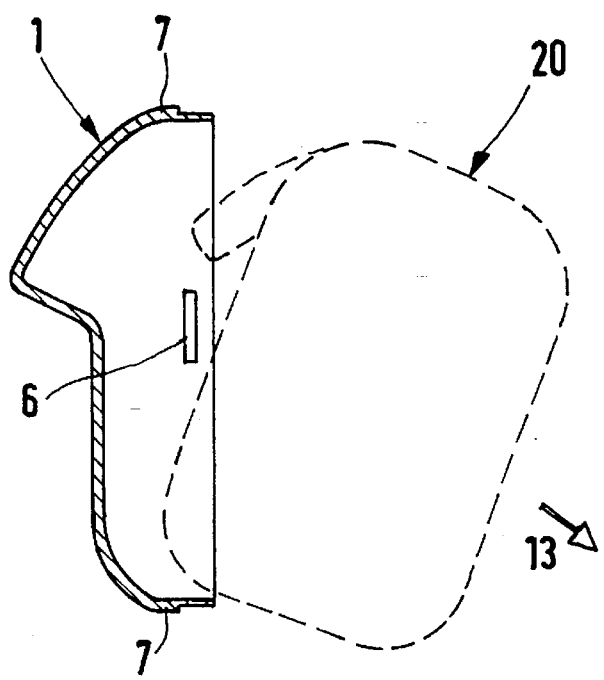
FIG. 4 schematically shows the removal of a capsule from a container having clamping surfaces.

In the sectional view of FIG. 1, the container is shown in the open condition prior to receiving a capsule. It consists of two shell portions 1, 2 and an intermediate ring 3. The size and shape of the inner space exactly correspond to those of the capsule (which is not shown for clarity) so that the capsule is snugly encompassed by the container. The shell portions join each other in an intermediate area where the capsule is located. Therefore, the capsule is exposed when the container is opened.

The ring 3 is fitted on the left-hand shell portion 1. The ring 3 and the left shell portion 1 are each provided with circumferential steps 10, 11, with the step 10 of the ring 3 engaging the corresponding step 11 of the left shell portion 1.

A circumferential nose 8 is formed on the right-hand outer edge of the ring 3 and engages behind a corresponding nose 9 of the right-hand shell portion 2 when the container is closed as shown in FIG. 2. Instead of circumferential noses 8 and 9, discrete noses may be provided.

In the closed condition, the right shell portion 2 overlaps the ring 3 on the outer side thereof, which ring 3 in turn overlaps the left-hand shell portion 1 on the outer side thereof in the area of the steps 10 and 11. As a result, a uniformly effective sealing force may be exerted on both ends of the ring 3. The ring 3 may be made of the same material as either one of the two shell portions 1, 2; advantageously, however, it should be more resilient than the shell portions. Moreover, the diameters of the parts are so dimensioned that the sealing contact surfaces are slightly compressed.

The closed container together with the inner capsule are sterilised most suitably by radioactive radiation and thereafter stored in a germ-impermeable sterile bag from which it is removed just shortly before it is used. The container stays sterile for a limited but sufficient period.

For actuating a capsule (not shown) inside the container, the two shell portions 1, 2 are compressed in the direction of the arrows 12 shown in FIG. 2. During this compression, the right shell portion 2 slides somewhat over the ring 3 and over the left shell portion 1, so that the compression force is transmitted to the interior capsule. Due to the shape of the steps 10 and 11 of the ring 3 and the left shell portion 1, these two parts do not move relatively to each other during actuation.

As a result of the container halves being moved against each other, the sealing surface of the right shell portion 2, which is identified by 5 in FIG. 1, slides on the outer side of the ring 3 and the left shell portion 1. The surface 5 is thus contaminated by germs and impurities that exist on the outer side of the container.

For opening the container, the two shell portions are pulled apart and completely separated. In order to protect the sterile capsule from contacting the surface 5 of the right shell portion 2, which is no longer sterile, the container cannot be opened at the junction between the ring 3 and the right-hand shell portion 2, at which the relative sliding movement took place. The noses 8 and 9 of the ring 3 and the right shell portion 2 rather cause these parts to remain hooked. Thus, when the left and right shell portions 1, 2 are pulled apart, the container opens between the left shell portion 1 and the ring 3, as shown in FIG. 3. The ring 3 remains connected to the right shell portion 2 and thus covers the inner sealing surface 5 of the right shell portion 2, which is no longer sterile.

As described, the ring 3 is fitted onto the left shell portion 1 and is removed therefrom when the container is opened. It is also possible that the two parts are integrally formed and then separated from each other at a weakened tearing location.

The left shell portion 1 shown in FIG. 4 has clamping surfaces 6 provided at two opposite inner sides, only one of which is shown in the sectional view. When the container is opened, the capsule 20 is retained between the clamping surfaces 6. By applying pressure on two other surfaces 7 of the shell portion 1, which are disposed transversely of the clamping surfaces 6, the shell portion 1 is deformed and the walls, which have the clamping surfaces 6 provided at their inner sides, bulge outwardly. The capsule is thus released and can be dropped in the direction of the arrow 13 onto a sterile tray or the like without requiring any contacting handling. This may be done for instance in a sterile sluice leading to the operating room. The capsule will then be passed on the tray into the operating room.

Figure 5:
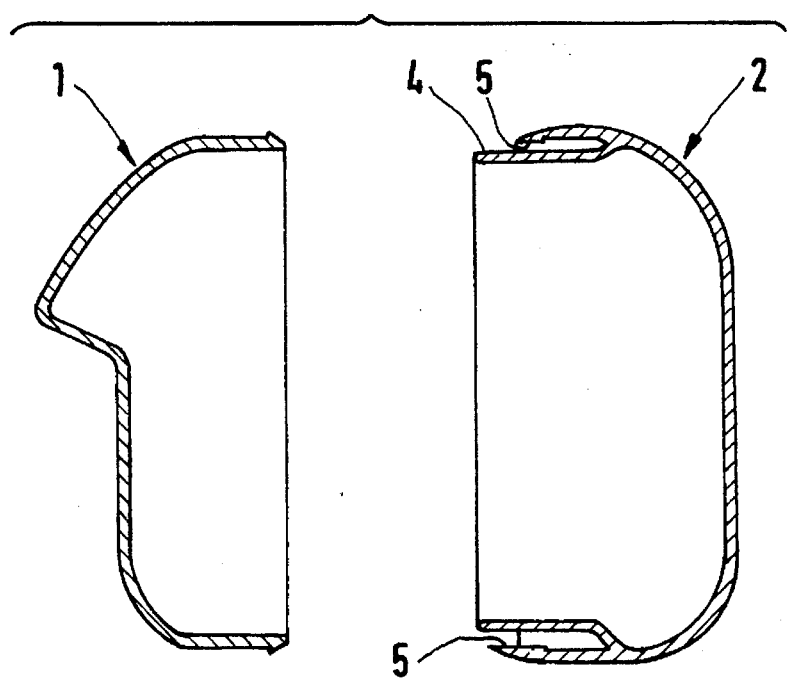
FIG. 5 illustrates a container provided with an apron according to a further embodiment.

In the container represented in FIG. 5, an apron 4 integrally formed on the right shell portion 2 fulfills the protecting function of the above-described ring 3. Otherwise, the handling of this container corresponds to that of the above embodiment. When pressure is applied, the two shell portions 1 and 2 move towards each other. During this movement, the inner sealing surface 5 of the right shell portion 2, which in the assembled condition overlaps the other shell portion 1 on the outside thereof, slides on the outer surface of the container and is thus contaminated. When the container is opened, the two shell portions are separated. The inner capsule (not shown) is then prevented by the apron 4 from contacting the sealing surface 5, which is no longer sterile.

The existence of the apron 4 causes the space available inside the container for receiving the capsule to be somewhat smaller than in the embodiment of FIGS. 1 to 4. On the other hand the container of FIG. 5 is advantageous in that the number of sealing surfaces is reduced and, particularly when the apron is formed integrally with the right shell portion 2 as shown, a smaller number of parts need be manufactured with the required precision.

In the embodiments described above, the container is opened by pulling the two shell portions 1 and 2 apart so that they are completely separated from each other. It is also conceivable for the shell portions to remain connected by a hinge or bending web.

The container is preferably made of transparent material so that the type of capsule received therein can be recognised from the outside. To this end, the capsule is suitably provided with a color coding.

I claim:

1. A container for receiving a pressure actuated sterile capsule, comprising:

two sterile-sealing shell portions adapted when interconnected to snugly surround the capsule, the interconnection of said shell portions being such that one of said shell portions is adapted to slide against the other of said shell portions so that when said shell portions are compressed, pressure is transmitted to said capsule, said one shell portion having a surface which, when said shell portions are compressed, slides over an exposed outer surface of said other shell portion, said shell portions upon opening being completely separable from each other, one of said shell portions being provided on an interior surface thereof with two opposite clamping surfaces for engaging the capsule, said clamping surfaces, when the container is opened, being adapted to be deformed by pressure exerted on opposed outer surfaces of said shell portion so as to release the capsule, and means for protecting the capsule against contact with said surface of said one shell portion when said shell portions are opened to permit removal of said capsule from the container.

2. A container for receiving a pressure-actuated sterile capsule, including two sterile-sealing shell portions adapted to slide against each other when compressed thereby transmitting pressure to the capsule, and to be opened for subsequent removal of the capsule, and means for protecting the capsule, when said shell portions are opened, against contact with that surface of one of said shell portions which, when said shell portions are moved against each other, slides on an outer surface of the other shell portion, and wherein said protecting means includes a ring provided between said shell portions, said ring being connected to said other shell portion and slidable with respect to said one shell portion when said shell portions are moved against each other, and being adapted to disengage from said other shell portion and remain connected to said one shell portion when said container is opened.

3. The container of claim 2, wherein said ring and said one shell portion are provided with cooperating noses which permit a sliding movement between these parts when compressed, said noses causing said ring and said one shell portion to become hooked together when said two shell portions are pulled apart.

* * * * *